United States Patent
Wang et al.

(10) Patent No.: US 9,931,431 B2
(45) Date of Patent: *Apr. 3, 2018

(54) IMPLANTABLE MEDICAL DEVICES FABRICATED FROM BRANCHED POLYMERS

(71) Applicant: Abbott Cardiovascular Systems Inc., Santa Clara, CA (US)

(72) Inventors: Yunbing Wang, Sunnyvale, CA (US); David C. Gale, Kennesaw, GA (US); Bin Huang, Pleasanton, CA (US); Mikael O. Trollsas, San Jose, CA (US); Thierry Glauser, Redwood City, CA (US); Florian Ludwig, Ebikon (CH)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 1073 days.

This patent is subject to a terminal disclaimer.

(21) Appl. No.: 13/941,374

(22) Filed: Jul. 12, 2013

(65) Prior Publication Data

US 2014/0046006 A1    Feb. 13, 2014

Related U.S. Application Data

(62) Division of application No. 11/784,886, filed on Apr. 9, 2007, now Pat. No. 8,486,135.

(60) Provisional application No. 60/810,302, filed on Jun. 1, 2006.

(51) Int. Cl.
| | |
|---|---|
| *A61F 2/82* | (2013.01) |
| *A61L 27/14* | (2006.01) |
| *A61L 27/18* | (2006.01) |
| *A61L 31/06* | (2006.01) |
| *C08L 67/04* | (2006.01) |

(52) U.S. Cl.
CPC .............. *A61L 27/14* (2013.01); *A61L 27/18* (2013.01); *A61L 31/06* (2013.01); *C08L 67/04* (2013.01)

(58) Field of Classification Search
CPC ............ A61F 2/82; A61F 2/20; A61K 9/0024
USPC ................................................ 623/1.15–1.48
See application file for complete search history.

(56) References Cited

U.S. PATENT DOCUMENTS

| | | | |
|---|---|---|---|
| 4,743,257 A * | 5/1988 | Tormala | ............... A61L 31/148 264/257 |
| 5,147,721 A * | 9/1992 | Baron | ..................... C03B 37/15 428/359 |
| 5,171,264 A | 12/1992 | Merrill | |
| 5,175,235 A | 12/1992 | Domb et al. | |

(Continued)

FOREIGN PATENT DOCUMENTS

| | | |
|---|---|---|
| EP | 1 473 316 | 11/2004 |
| JP | 2000-006142 | 1/2000 |

(Continued)

OTHER PUBLICATIONS

Asplund Basse et al., "Effects of hydrolysis on a new biodegradable co-polymer", J. of Biomaterials Science Polymer Edition, VSP, UTRECHT vol. 17, pp. 615-630 (2006).

(Continued)

*Primary Examiner* — Suzette J Gherbi
(74) *Attorney, Agent, or Firm* — Squire Patton Boggs (US) LLP

(57) ABSTRACT

Implantable medical devices fabricated from branched polymers are disclosed.

21 Claims, 3 Drawing Sheets

(56) References Cited

U.S. PATENT DOCUMENTS

| | | | |
|---|---|---|---|
| 5,275,838 A | 1/1994 | Merrill | |
| 5,840,814 A | 11/1998 | Majoros et al. | |
| 6,380,303 B1* | 4/2002 | Ogoe | C08F 279/02 525/67 |
| 6,528,080 B2 | 3/2003 | Dunn et al. | |
| 6,924,347 B2 | 8/2005 | Morgan et al. | |
| 7,056,339 B2 | 6/2006 | Elkins et al. | |
| 7,241,455 B2* | 7/2007 | Richard | A61K 9/0024 424/423 |
| 7,517,914 B2* | 4/2009 | Richard | A61K 9/0024 514/772.1 |
| 7,794,495 B2* | 9/2010 | Gale | A61L 31/06 528/354 |
| 7,879,356 B2 | 2/2011 | Cohn et al. | |
| 8,262,723 B2* | 9/2012 | Wang | A61L 27/48 623/1.38 |
| 8,293,260 B2 | 10/2012 | Wang | |
| 8,486,135 B2 | 7/2013 | Wang et al. | |
| 8,512,736 B2 | 8/2013 | Chudzik et al. | |
| 8,691,912 B2 | 4/2014 | Suzuki et al. | |
| 9,265,866 B2 | 2/2016 | Kramer-Brown et al. | |
| 2002/0032298 A1 | 3/2002 | Bennett et al. | |
| 2002/0071822 A1* | 6/2002 | Uhrich | A61K 47/48023 424/78.37 |
| 2003/0195610 A1* | 10/2003 | Herrmann | A61L 31/10 623/1.15 |
| 2004/0086479 A1 | 5/2004 | Grinstaff et al. | |
| 2004/0131582 A1 | 7/2004 | Grinstaff et al. | |
| 2004/0231187 A1 | 11/2004 | Moretto | |
| 2005/0137381 A1* | 6/2005 | Pacetti | A61L 27/34 528/272 |
| 2005/0149173 A1 | 7/2005 | Hunter et al. | |
| 2006/0095122 A1* | 5/2006 | Pacetti | A61L 31/10 623/1.46 |
| 2006/0184092 A1 | 8/2006 | Atanasoska et al. | |
| 2007/0178135 A1 | 8/2007 | Zhong | |
| 2007/0244549 A1 | 10/2007 | Pathak | |
| 2007/0283552 A1 | 12/2007 | Gale et al. | |
| 2007/0298069 A1 | 12/2007 | Bucay-Couto et al. | |
| 2008/0015686 A1 | 1/2008 | Gale et al. | |
| 2008/0050413 A1 | 2/2008 | Horvers et al. | |
| 2008/0177102 A1 | 7/2008 | Zhao | |
| 2008/0268013 A1 | 10/2008 | Chaikof et al. | |
| 2008/0275210 A1 | 11/2008 | Zhao | |
| 2009/0149941 A1 | 6/2009 | Hasson et al. | |
| 2011/0022163 A1 | 1/2011 | Wang et al. | |
| 2011/0174434 A1 | 7/2011 | Hsiao | |
| 2014/0081417 A1 | 3/2014 | Wang et al. | |
| 2014/0110885 A1 | 4/2014 | Wang et al. | |
| 2014/0364575 A1 | 12/2014 | Wang | |
| 2016/0030212 A1 | 2/2016 | Stankus et al. | |

FOREIGN PATENT DOCUMENTS

| | | |
|---|---|---|
| JP | 2003-206348 | 7/2003 |
| JP | 2008-260280 | 10/2008 |
| JP | 2009-538688 | 11/2009 |
| JP | 2010-195867 | 9/2010 |
| JP | 2012-139835 | 7/2012 |
| JP | 2012-533407 | 12/2012 |
| WO | WO 99/02168 | 1/1999 |
| WO | WO 02/096967 | 12/2002 |
| WO | WO 2007/142752 | 12/2007 |
| WO | WO 2011/011241 | 1/2011 |

OTHER PUBLICATIONS

Buschnakowski M. et al., "Influence of phase separation behaviour on toughness of compression moulded SBS star block copolymer / polystyrene blends", Macromolecular Symposia vol. 233, pp. 66-77 (2006).

International Search Report for PCT/US2007/012981, mailed Jun. 27, 2008, 5 pgs.

Office Action mailed Jun. 17, 2009 in European Patent Application No. 07795624.1, 4 pages.

Office Action mailed May 31, 2016 in Japanese Patent Application No. P2014-525089, 9 pages.

Non-Final Office Action mailed Sep. 29, 2016 in U.S. Appl. No. 14/084,427, 9 pages.

* cited by examiner

IMPLANTABLE MEDICAL DEVICES FABRICATED FROM BRANCHED POLYMERS

CROSS REFERENCE TO RELATED APPLICATION

This application is a divisional of application Ser. No. 11/784,886, filed Apr. 9, 2007, which claims the benefit of Application No. 60/810,302, filed Jun. 1, 2006, both of which applications are incorporated herein by reference.

BACKGROUND OF THE INVENTION

Field of the Invention

This invention relates to implantable medical devices fabricated from polymer blends including branched polymers.

Description of the State of the Art

This invention relates to radially expandable endoprostheses, which are adapted to be implanted in a bodily lumen. An "endoprosthesis" corresponds to an artificial device that is placed inside the body. A "lumen" refers to a cavity of a tubular organ such as a blood vessel.

A stent is an example of such an endoprosthesis. Stents are generally cylindrically shaped devices, which function to hold open and sometimes expand a segment of a blood vessel or other anatomical lumen such as urinary tracts and bile ducts. Stents are often used in the treatment of atherosclerotic stenosis in blood vessels. "Stenosis" refers to a narrowing or constriction of the diameter of a bodily passage or orifice. In such treatments, stents reinforce body vessels and prevent restenosis following angioplasty in the vascular system. "Restenosis" refers to the reoccurrence of stenosis in a blood vessel or heart valve after it has been treated (as by balloon angioplasty, stenting, or valvuloplasty) with apparent success.

The treatment of a diseased site or lesion with a stent involves both delivery and deployment of the stent. "Delivery" refers to introducing and transporting the stent through a bodily lumen to a region, such as a lesion, in a vessel that requires treatment. "Deployment" corresponds to the expanding of the stent within the lumen at the treatment region. Delivery and deployment of a stent are accomplished by positioning the stent about one end of a catheter, inserting the end of the catheter through the skin into a bodily lumen, advancing the catheter in the bodily lumen to a desired treatment location, expanding the stent at the treatment location, and removing the catheter from the lumen.

In the case of a balloon expandable stent, the stent is mounted about a balloon disposed on the catheter. Mounting the stent typically involves compressing or crimping the stent onto the balloon. The stent is then expanded by inflating the balloon. The balloon may then be deflated and the catheter withdrawn. In the case of a self-expanding stent, the stent may be secured to the catheter via a constraining member such as a retractable sheath or a sock. When the stent is in a desired bodily location, the sheath may be withdrawn which allows the stent to self-expand.

The stent must be able to satisfy a number of mechanical requirements. First, the stent must be capable of withstanding the structural loads, namely radial compressive forces, imposed on the stent as it supports the walls of a vessel. Therefore, a stent must possess adequate radial strength. Radial strength, which is the ability of a stent to resist radial compressive forces, is due to strength and rigidity around a circumferential direction of the stent. Radial strength and rigidity, therefore, may also be described as, hoop or circumferential strength and rigidity.

Once expanded, the stent must adequately maintain its size and shape throughout its service life despite the various forces that may come to bear on it, including the cyclic loading induced by the beating heart. For example, a radially directed force may tend to cause a stent to recoil inward. Generally, it is desirable to minimize recoil. In addition, the stent must possess sufficient flexibility to allow for crimping, expansion, and cyclic loading. Longitudinal flexibility is important to allow the stent to be maneuvered through a tortuous vascular path and to enable it to conform to a deployment site that may not be linear or may be subject to flexure. Finally, the stent must be biocompatible so as not to trigger any adverse vascular responses.

The structure of a stent is typically composed of scaffolding that includes a pattern or network of interconnecting structural elements often referred to in the art as struts or bar arms. The scaffolding can be formed from wires, tubes, or sheets of material rolled into a cylindrical shape. The scaffolding is designed so that the stent can be radially compressed (to allow crimping) and radially expanded (to allow deployment). A conventional stent is allowed to expand and contract through movement of individual structural elements of a pattern with respect to each other.

Additionally, a medicated stent may be fabricated by coating the surface of either a metallic or polymeric scaffolding with a polymeric carrier that includes an active or bioactive agent or drug. Polymeric scaffolding may also serve as a carrier of an active agent or drug.

Furthermore, it may be desirable for a stent to be biodegradable. In many treatment applications, the presence of a stent in a body may be necessary for a limited period of time until its intended function of, for example, maintaining vascular patency and/or drug delivery is accomplished. Therefore, stents fabricated from biodegradable, bioabsorbable, and/or bioerodible materials such as bioabsorbable polymers should be configured to completely erode only after the clinical need for them has ended.

Potential problems with polymeric implantable medical devices, such as stents, include insufficient toughness, slow degradation rate, and limited shelf life due to physical aging and stress relaxation.

SUMMARY OF THE INVENTION

Various embodiments of the present invention include a stent fabricated at least in part from a polymeric material comprising a branched biodegradable polymer, the structure of the branched biodegradable polymer selected from the group consisting of hyperbranched-like polymers, comb-like polymers, star polymers, dendrimer-like star polymers, dendrimers, or any mixture thereof in any proportion.

Further embodiments of the present invention include a stent fabricated from a polymeric material comprising an unbranched biodegradable polymer blended with a branched biodegradable polymer, wherein a majority of the polymeric material comprises the unbranched polymer.

Additional embodiments of the present invention include an implantable medical device fabricated from a polymeric material, the polymeric material comprising a polymer blend including: a matrix polymer blended with star-block copolymers having at least three arms, wherein the arms include inner segments and outer segments, the inner segments forming a discrete phase within a continuous phase, the continuous phase including the matrix polymer and the outer segments.

Other embodiments of the present invention include a method of fabricating an implantable medical device comprising: forming star-block copolymers having at least three arms, wherein the arms include inner segments and outer segments; blending a matrix polymer with the star-block copolymers, wherein the blend comprises discrete phase regions dispersed within the continuous phase, the continuous phase comprising the matrix polymer and the outer segments, the discrete phase regions comprising the inner segments; and fabricating an implantable medical device from the blend.

DETAILED DESCRIPTION OF THE INVENTION

Various embodiments of the present invention include an implantable medical device fabricated from a polymeric material including branched structured polymers. Certain embodiments include an implantable medical device fabricated from a polymer blend of a matrix polymer and a star-block copolymer, which includes a discrete polymer phase within a continuous phase.

As used herein, an "implantable medical device" includes, but is not limited to, self-expandable stents, balloon-expandable stents, stent-grafts, other expandable tubular devices for various bodily lumen or orifices, implantable cardiac pacemakers and defibrillators, leads and electrodes for the preceding, vascular grafts, grafts, artificial heart valves, and cerebrospinal fluid shunts. An implantable medical device can be designed for the localized delivery of a therapeutic agent. A medicated implantable medical device may be constructed by coating the device or substrate with a coating material containing a therapeutic agent. The substrate of the device may also contain a therapeutic agent.

Figure 1A:
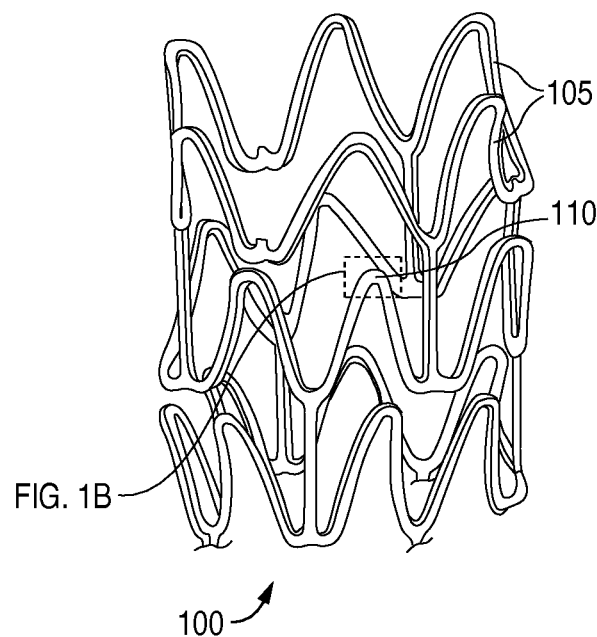
FIG. 1A depicts a view of a stent.

FIG. 1A depicts a view of a stent 100. In some embodiments, a stent may include a pattern or network of interconnecting structural elements 105. Stent 100 may be formed from a tube (not shown). The pattern of structural elements 105 can take on a variety of patterns. The structural pattern of the device can be of virtually any design. The embodiments disclosed herein are not limited to stents or to the stent pattern illustrated in FIG. 1A. The embodiments are easily applicable to other patterns and other devices. The variations in the structure of patterns are virtually unlimited. A stent such as stent 100 may be fabricated from a tube by forming a pattern with a technique such as laser cutting or chemical etching.

An implantable medical device can be made partially or completely from a biodegradable, bioabsorbable, biostable polymer, or a combination thereof. A polymer for use in fabricating an implantable medical device can be biostable, bioabsorbable, biodegradable or bioerodible. Biostable refers to polymers that are not biodegradable. The terms biodegradable, bioabsorbable, and bioerodible are used interchangeably and refer to polymers that are capable of being completely degraded and/or eroded when exposed to bodily fluids such as blood and can be gradually resorbed, absorbed, and/or eliminated by the body. The processes of breaking down and absorption of the polymer can be caused by, for example, hydrolysis and metabolic processes.

Some polymers that may be suitable for implantable medical devices such as stents, have potential shortcomings. One shortcoming is that polymers may have inadequate modulus and strength for certain applications. The strength to weight ratio of polymers is smaller than that of metals. To compensate, a polymeric stent may require significantly thicker struts than a metallic stent, which results in an undesirably large profile.

Another potential shortcoming of polymer devices is limited shelf life due to physical aging and stress relaxation. These processes occur as a result of creep, which is gradual deformation that occurs in a polymeric construct. On the molecular level, creep results from relaxation of polymer chains. One way of describing chain relaxation is through a process of called reptation. In a reptation model, the movement or path of the polymer chains is depicted as through a tunnel.

Various embodiments of the present invention reduce or eliminate such shortcomings. Certain embodiments of the present invention include a stent fabricated from a polymeric material including a branched biodegradable polymer. In general, a branched polymer corresponds to a polymer with "side chains." Branched polymers include, for example, hyperbranched-like polymers, comb-like polymers, star polymers, dendrimer-like star polymers, and dendrimers. A star-shaped polymer refers to a polymer having at least three chains or arms radiating outward from a common center. A dendritic polymer is a branched polymer resembling a tree-like structure. A comb structure corresponds to a linear polymer segment or backbone having a plurality of side chains extending outward from a position along the linear segment. In the embodiments described herein, the various polymer structures include a plurality of hydrolytically degradable functional groups or units.

It is believed that the process of reptation is reduced in polymeric materials that include branched polymers, which reduces creep of the material. Thus, a medical device including branched polymers should experience reduced physical aging and stress relaxation.

Additionally, it is also believed that branched polymers increase the strength of a polymer material. The chemical connectivity provided by the branched polymers can increase the strength of the polymeric material. The segments of the branched polymers may increase strength and stability of a polymer by acting as chemical net points, by increased entanglement, or both. Furthermore, it is expected that as a polymer degrades or absorbs, the degradation of mechanical properties, such as strength, is reduced due to the presence of branched polymers. Thus, a device made from a polymer including branched polymers is expected to maintain mechanical stability longer as it degrades.

In some embodiments, the branched polymers of the polymeric material can be homopolymers or copolymers. The copolymers can be random or block copolymers. In addition, the polymeric material can include one or more types of branched polymers. In some embodiments, the mechanical properties or degradation rate of the branched polymer can be controlled or tailored though its chemical composition. In one embodiment, the degradation rate of a branched copolymer can be increased by having a higher percentage of a unit that is more hydrolytically active. For example, the degradation rate of poly(L-lactide-co-glycolide) (LPLG) branched polymer can be increased by increasing the percentage of glycolide. In a similar manner, the toughness of a branched polymer can be controlled through the composition of units that form rubbery or elastomeric segments.

In certain embodiments, all or substantially all of the polymeric material of the stent is fabricated from a branched polymer. In other embodiments, a portion of the polymeric material of the stent includes a branched polymer. In some embodiments, the mechanical or degradation properties of the polymeric material can be tuned by varying the weight percent of branched polymers in the polymeric material. The weight percent of branched polymer in the polymeric material of the stent can be as high as 0.05 wt %, 1 wt %, 10 wt %, 30 wt %, 50 wt %, 70 wt %, 90 wt %, or 95 wt %.

In additional embodiments, the molecular weight of branched polymers can be used to tailor the mechanical and degradation properties of a polymeric material of a stent. In another embodiment, the molecular weight distribution of branched polymers can be used to control mechanical and degradation properties. The molecular weight distribution can be monodisperse, broad, bimodal, or multimodal. Properties of a monodisperse polymer may tend to change rapidly over a short time frame. Alternatively, properties of a polymer with a broad molecular weight distribution may change more gradually. A polymer with a bimodal or multimodal distribution may exhibit changes in properties in stages.

In additional embodiments, the chemical composition of branches of branched polymer of the polymeric material can be the same or different. In other embodiments, the molecular weight of branches can also be different. Thus, the mechanical and degradation properties of the polymeric material may be tailored by having branches with different chemical composition, molecular weight, or both.

Branched polymers are known one of ordinary skill in the art. For example, various kinds of branched polymer and synthesis and characterization of branched polymers can be found in U.S. Pat. No. 6,207,767; U.S. Pat. No. 6,231,960; U.S. Pat. No. 5,399,666; U.S. Pat. No. 5,225,521; U.S. Pat. No. 6,316,590; Lowenhielm et al., *Macromol. Chem. Phys,* 2004, 205, 1489-1496; Trollsas, M. et al., "*Layered Dendritic Block Copolymers,*" Angew. Chem., Int. Ed. Engl. 1998, 110, 3308; Trollsas, M. et al., "*Internal functionalization in hyperbranched polyesters,*" J. Polym. Sci., Chem. Ed. 1998, 36, 3187; Trollsas M. et al., "*Dendrimer-like Starpolymers,*" J. Am. Chem. Soc. 1998, 120, 4644; Trollsas, M. et al., "*Highly branched block copolymers: Design, synthesis and morphology,*" Macromolecules, 1999, 32, 4917; Trollsas, M. et al., "*Constitutional isomers of dendrimer-like starpolymers,*" Macromolecules, 2000, 33, 6423; Trollsas, M. et al., "*Dendritic homopolymers and block copolymers: Tuning the morphology and properties,*" J. Polym. Sci., Chem. Ed. 2004, 42, 1174, Ihre et al., *Macromolecules* 1996, 118, 6388; and Johansson et al., *J. Polym Sci., Polym. Chem.* 1993, 31, 619.

Branched polymers of the polymeric material can include, but are not limited to, polylactide, polyglycolide, poly (lactic-co-glycolic acid), poly(ε-caprolactone), poly(trimethylene carbonate), poly(hydroxy butyrate), polydioxanone, poly(orthoesters) poly(ethylene carbonate), poly (propylene carbonate), poly(amides), poly(phosphoesters), poly(phosphazenes), poly(anhydrides) and any blends or copolymers thereof. Branched polymers can also include polyester amides, polypeptides, polyethylene glycol, polyacrylates, polymethacrylates, polypropylene oxides, polysaccharides, and any blends or copolymers thereof.

In some embodiments, a multi-arm star polymer can be used as a viscosity modifier to reduce the viscosity during melt processing of a polymer. In order to melt process a biodegradable polymer, the temperature of the polymer is increased to reduce the viscosity to allow flow of the polymer. To process high molecular weight polymers that, it may be necessary process at a very high temperatures which can cause degradation of the polymer. For example, high molecular weight poly(L-lactide) (PLLA) with molecular weight in the range from 100 kD to 800 kD is extruded at temperatures between 400° F. to 440° F. The degradation of the polymer is accelerated in this temperature range.

It has been observed that multi-arm star copolymers can act as viscosity modifiers in melt processing of a polymer. Progr. Polym. Sci. 29, 2004, 183-275. Incorporating a multi-arm star copolymer with PLLA in melt processing reduces the viscosity of the polymer melt. As a result, the polymer can be processed at a lower temperature which reduces the amount of molecular weight degradation of the polymer during processing. In some embodiments, a multi-arm star copolymer can be blended into a polymer before, during, or after melt processing the polymer for an implantable medical device. In an embodiment, the multi-arm star copolymer can be composed of the same units as the polymer. In another embodiment, the multi-arm star copolymer can be composed of different units than the polymer. The multi-arm star copolymer can be less than 0.05 wt %, 1 wt %, 2 wt %, 5%, or less than 20 wt % of the blend.

Further embodiments of the present invention can include an implantable medical device fabricated from a polymer blend having a discrete phase within a continuous phase. In some embodiments, the polymer blend includes a matrix polymer blended with a star-block copolymer having at least three arms. In an embodiment, the arms include inner core segments and outer segments with the inner segments being immiscible with the outer segments and the matrix polymer. The inner segments form a discrete phase with the continuous phase which includes the matrix polymer and the outer segments. The star-block copolymer can be dispersed throughout the matrix polymer so that there are a plurality of discrete phase regions within the blend. A majority of the polymer blend includes the matrix polymer.

These embodiments can address additional shortcomings of polymers for relating to implantable medical devices. For example, some biodegradable polymers have a degradation rate that is slower than desired for certain stent treatments. As a result, the degradation time of a stent made from such polymers can be longer than desired. For example, a stent made from a semi-crystalline polymer such as PLLA can have a degradation time between about two and three years. In some treatment situations, a shorter degradation time is desirable, for example, less than 6 months or a year.

An additional shortcoming of some polymers is that their toughness can be lower than desired, in particular, for use in stent applications. As indicated above, it is important for a stent to have high radial strength and stiffness so that it can support a lumen. Some crystalline or semi-crystalline polymers that are glassy or have a Tg above body temperature are particularly attractive as stent materials due to their strength and stiffness. Some of these polymers, that may be suitable for implantable medical devices such as stents, have potential shortcomings. One shortcoming of such polymers is that their toughness can be lower than desired, in particular, for use in stent applications. For example, polymers such as PLLA are stiff and strong, but tend to be brittle under physiological conditions. Physiological conditions refer to conditions that an implant is exposed to within a human body. Physiological conditions include, but are limited to, human body temperature, approximately 37° C. These polymers can exhibit a brittle fracture mechanism at these conditions in which there is little or no plastic deformation prior to failure. As a result, a stent fabricated from such polymers can have insufficient toughness for the range of use of a stent.

One way to increase fracture toughness of a matrix polymer is to blend it with a polymer having a higher or relatively high fracture toughness under physiological conditions, for example, a rubbery polymer or elastomer. The higher fracture toughness polymer should also be immiscible with the matrix polymer so that it forms a discrete or dispersed phase within the matrix polymer phase. However, the discrete or dispersed phase should be interfacially compatible with the matrix phase to reduce or eliminate the formation of voids at the interface of the phases when the polymer blend is under stress, for example, when a stent is expanded. The fracture toughness of a device is increased since the discrete phase can absorb energy arising from stress imparted to a device. To ensure good energy transfer between interfaces of the phases, it is important that there be sufficient bonding or adhesion between the phases. See, Y. Wang, etc. Journal of Polymer Science Part A: Polymer Chemistry, 39, 2001, 2755-2766.

In some embodiments, the matrix polymer has a high rigidity and a relatively low fracture toughness at physiological conditions. Such polymers may be selected as a matrix polymer for stent applications since such rigid polymers can support the walls of a vessel. The discrete phase inner segment can have a higher fracture toughness at physiological conditions. The discrete phase inner segments tend to increase the toughness of the polymer blend. The outer segments improve adhesion between the continuous and discrete phases to facilitate energy transfer between the phases.

Figure 1B:
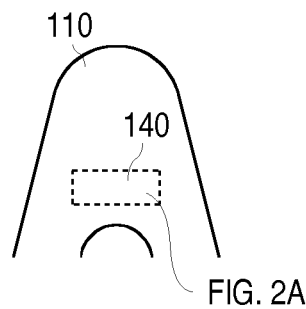
FIG. 1B depicts a section of a structural element from the stent depicted in FIG. 1A.
Figure 2:
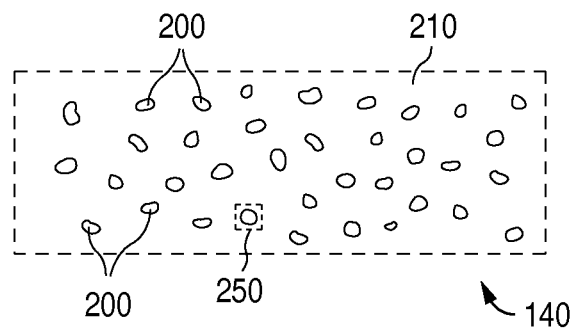
FIG. 2 depicts a schematic close-up view of the section depicted in FIG. 1B.

FIG. 1B depicts a section of a segment 110 of strut 105 from the stent depicted in FIG. 1A. FIG. 2 depicts a microscopic schematic view of a portion 140 of segment 110 of a strut as depicted in FIG. 1B. Portion 140 includes a plurality of discrete phase regions 200 dispersed within a continuous phase 210.

Figure 3:
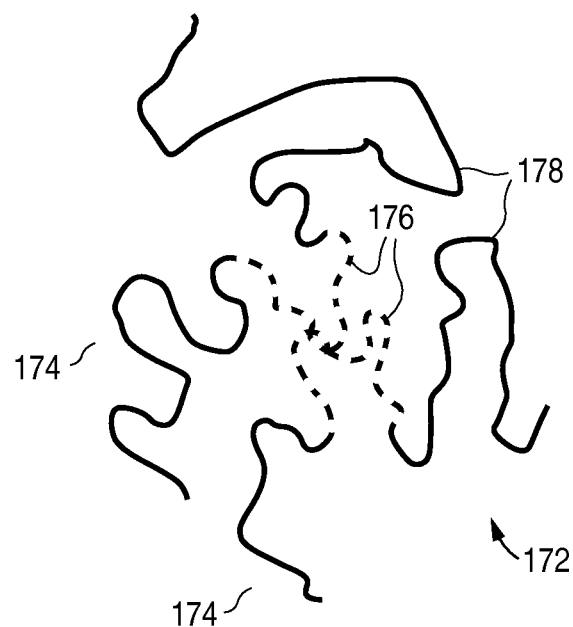
FIG. 3 depicts a star-block copolymer having four arms.

FIG. 3 depicts a star-block copolymer 172 having four arms 174. Arms 174 have inner segments 176 (shown as broken lines) and outer segments 178. Inner segments 176 are discrete phase blocks and outer segments 178 are continuous phase blocks.

Figure 4:
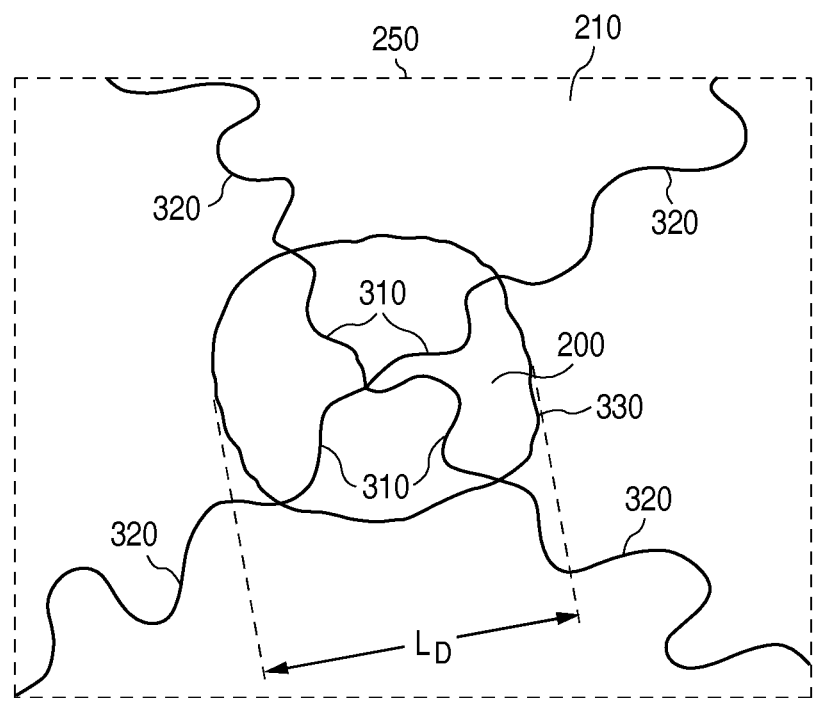
FIG. 4 depicts a schematic close-up view of a discrete polymer phase dispersed within a continuous polymer phase.

FIG. 4 depicts a schematic close-up view of section 250 of FIG. 2 of a discrete phase region 200 and the interface between discrete phase region 200 and continuous polymer phase 210. Section 250 includes a star-block copolymer with inner core segments 310 and outer segments 320. Line 330 delineates an approximate boundary between discrete phase region 200 and continuous phase 210. $L_D$ is a characteristic dimension of discrete phase region 200. For clarity, matrix polymer segments are not shown in continuous phase 200.

It is believed that when a device is placed under stress, the discrete phase tends to absorb energy when a fracture starts to propagate through a structural element. Crack propagation through the continuous phase may then be reduced or inhibited. As a result, fracture toughness of the polymer blend, and thus, the implantable medical device tends to be increased. The outer segments anchor the discrete phase regions within the matrix polymer, increasing the adhesion between the discrete phase and the continuous phase. Thus, the outer segments facilitate energy transfer between interfaces of the phases. Without the anchoring or adhesion provided by the outer segments, a propagating crack may go around the discrete phase, reducing the effectiveness of the discrete phase in absorbing energy imparted to a device.

Generally, it is desirable for the discrete phase regions to be uniformly or substantially uniformly dispersed throughout the polymer matrix to facilitate the increase in toughness. The more dispersed the discrete phase regions, the greater is the increase in toughness. Additionally, the increase in toughness is related to the size of the discrete phase. Both the degree of dispersion and discrete phase size can be controlled by the length or molecular weight of the discrete phase inner segments. The characteristic length of a discrete phase can be 1 nm to 100 nm, 100 nm to 500 nm, 500 nm to 1,000 nm, 1000 nm to 10,000 nm, or greater than 10,000 nm. The molecular weight of the inner segments can be adjusted to obtain a desired characteristic length. It can be 10-50 kD, 50-100 kD, or higher than 100 kD.

In general, the outer segments can be selected so that they are miscible with the matrix polymer. In some embodiments, the outer segments can be the same chemical composition as the matrix polymer. For example, a polymer blend with a PLLA matrix polymer can have PLLA outer segments. In some embodiments, the matrix polymer can be a copolymer having a high percentage of L-lactide units, for example, the L-lactide copolymer can have at least 80 weight percent of L-lactide units.

In some embodiments, the inner segments of the star-block copolymer include units that are form polymers having a higher fracture toughness at physiological conditions than a rigid matrix polymer, such as PLLA. The discrete phase inner segments can form a discrete phase that is more flexible and has a lower modulus than the matrix polymer of the continuous phase. The matrix polymer can be selected to have a Tg above body temperature, so that the matrix polymer remains rigid after implantation. Generally, the discrete phase inner segments may be selected that have a Tg below body temperature. In one embodiment, the discrete phase segments of the star-block polymer can be a rubbery or elastomeric polymer. An "elastomeric" or "rubbery" polymer refers to a polymer that exhibits elastic deformation though all or most of a range of deformation. In some embodiments, the discrete phase can be substantially or completely amorphous.

Biodegradable polymers having a relatively high fracture toughness at body temperature include, but are not limited to, polycaprolactone (PCL), poly(tetramethyl carbonate) (PTMC), poly(4-hydroxy butyrate), and polydioxanone. Thus, some embodiments of the discrete phase inner segments of the star-block polymer can include caprolactone (CL), tetramethyl carbonate (TMC), 4-hydroxy butyrate, dioxanone units, or a combination thereof.

In one embodiment, a polymer blend can have a PLLA matrix polymer with P(CL-co-TMC)-b-PLLA star-block copolymer dispersed within the PLLA matrix. The discrete phase inner segment is P(CL-co-TMC) and the outer segments are PLLA. The PLLA outer segments of the star-block copolymer for a continuous matrix phase. The PLLA outer segment binds the discrete phase with the continuous phase, facilitating the increase in the fracture toughness provided to the polymer blend. In exemplary embodiments, the polymer blend can include about 1-30 wt %, or more narrowly, 5-20 wt % of a star-block copolymer and about 75-95 wt % of matrix polymer.

Furthermore, a device fabricated from embodiments of the polymer blends can address issues relating to the degradation rate of polymer devices. As indicated above, a matrix polymer, such as PLLA, can have a degradation rate that is slower than desired for certain stent treatments. The slow degradation rate is due at least in part to the crystallinity of a matrix polymer. In some embodiments, the discrete phase inner segments of the star-block copolymer can be faster degrading that the matrix polymer. The faster degradation can be due at least in part to the amorphous structure of the discrete phase since the diffusion rate of fluids through an amorphous structure is generally faster than through a crystalline structure. The faster degrading inner segments increase water penetration and content in the discrete phase and in the continuous phase. The increased water penetration and content causes an increase in the degradation rate of the blend, and thus, the device.

In additional embodiments, the star-block copolymer can include units in the discrete phase inner segments with characteristics that tend to increase the degradation rate of the blend. For example, the discrete phase inner segments can include units that are more hydrophilic than the matrix polymer. The discrete phase inner segments can also have units that are more hydrolytically active than the matrix polymer. These two characteristics increase the moisture content of the polymer blend which increases the degradation rate of the blend. Additionally, the discrete phase inner segments can also have units that have acidic and hydrophilic degradation products. Since the rate of the hydrolysis reaction tends to increase as the pH decreases, acidic degradation products can increase the degradation rate of the blend and the device. Glycolide (GA) units, for example, have acidic degradation products which can increase the degradation rate of a polymer blend when included in a discrete phase inner segment.

In some embodiments, the discrete phase inner segments can include units that increase the fracture toughness (toughness-enhancing units) of the polymer blend and units that have one or more of the characteristics that increase degradation rate mentioned above (fast degrading units). In an exemplary embodiment, the discrete phase inner segments can include both CL and GA units. In particular, the discrete phase inner segments can be poly(glycolide-co-ε-caprolactone) (P(GA-co-CL)). P(GA-co-CL) discrete phase inner segments can have alternating or random GA and CL units.

An exemplary star-block copolymer for blending with PLLA can include PLLA-b-P(CL-co-GA). The faster degrading GA units can increase the degradation rate of the polymer blend by increasing the equilibrium water content and penetration into the structural element. Degradation of GA units further increases the degradation rate due to the acidic and hydrophilic degradation products.

In some embodiments, the flexibility and degradation rate of the discrete phase inner segments can be adjusted by the ratio of fast degrading and toughness-enhancing units. As the ratio of CL, for example, increases in P(GA-co-CL) segments, the star-block copolymer becomes more flexible and tougher. The Tg of the discrete phase inner segments can be tuned to a desired value by adjusting the ratio of component monomers. For example, the Tg of the discrete phase may be engineered to be less than a body temperature to provide a more flexible discrete phase under physiological conditions. Additionally, the degradation rate of the discrete phase inner segments, and thus the blend, can be increased by increasing the fraction of GA in the discrete phase inner segments. In exemplary embodiments, the P(GA-co-CL) segments can have up to 1 wt %, 5 wt %, 20 wt %, 50 wt %, 70 wt %, 80 wt %, or 90 wt % GA units.

In an exemplary embodiment, a polymer blend can have a PLLA matrix polymer with P(GA-co-CL)-b-PLLA star-block copolymer dispersed within the PLLA matrix. The discrete phase inner segments are P(GA-co-CL) and the outer segments are PLLA. The PLLA outer segments of the star-block copolymer phase separate into the PLLA matrix of the continuous matrix phase. The PLLA outer segment binds the discrete phase with the continuous phase, facilitating the increase in the fracture toughness provided to the polymer blend. In exemplary embodiments, the polymer blend can include about 1-30 wt %, or more narrowly, 5-20 wt % of a star-block copolymer and about 75-95 wt % of matrix polymer.

In further embodiments, the matrix polymer can be a copolymer. In some embodiments, a matrix copolymer can be composed of a primary functional group and at least one additional secondary functional group. The copolymer matrix may be a random copolymer including the primary functional group and at least one additional secondary functional group. In an embodiment, the copolymer with at least one secondary functional group can have a higher degradation rate than a homopolymer composed of the primary functional group. A secondary functional group can have a greater affinity for water or be more hydrolytically active than the secondary functional group. The secondary functional group can have acidic and hydrophilic degradation products that enhance the degradation of the matrix polymer and polymer blend. Additionally, a copolymer matrix may have lower crystallinity, which also tends to increase degradation rate. In some exemplary embodiments, the weight percent of the secondary functional group in the copolymer can have up to 1%, 5%, 10%, 15%, 30%, 40%, or, at least about 50%. In some embodiments, the weight percent of the secondary function group can be greater than 50%.

In an exemplary embodiment, the matrix copolymer can be poly(L-lactide-co-glycolide) (LPLG). The primary functional group can be L-lactide and the secondary functional group can be GA. The weight percent of the GA in the copolymer can be up to 1%, 5%, 10%, 15%, 30%, 40%, or at least about 50%. In certain exemplary embodiments, the weight percent of the GA group can be adjusted so that the degradation time of a stent, can be less than 18 months, 12 months, 8 months, 5 months, 3 months, or more narrowly, less than 3 months.

Additionally, the outer segments of the star-block copolymer can be selected so that the outer segments are miscible with the matrix copolymer. In one embodiment, the outer segment can have the same chemical composition as the matrix copolymer. In another embodiment, the outer segment can have a composition different from the matrix copolymer, but close enough so that the outer segment is miscible with the matrix polymer. In another embodiment, the outer segments can have a composition different from the matrix polymer with the outer segments being miscible with the matrix polymer.

In another exemplary embodiment, a polymer blend can have a LPLG matrix polymer with P(CL-co-TMC)-b-LPLG star-block copolymer dispersed within the LPLG matrix. The discrete phase inner segments are P(CL-co-TMC) and the outer segments are LPLG. The LPLG outer segments of the star-block copolymer phase separate into the LPLG matrix of the continuous matrix phase. The LPLG outer segment binds the discrete phase with the continuous phase, facilitating the increase in the fracture toughness provided to the polymer blend. In exemplary embodiments, the polymer blend can include about 1-30 wt %, or more narrowly, 5-20 wt % of a star-block copolymer and about 75-95 wt % of matrix polymer.

In a further exemplary embodiment, a polymer blend can have an LPLG matrix polymer with P(GA-co-CL)-b-LPLG star-block copolymer dispersed within the LPLG matrix. The discrete phase inner segments are P(GA-co-CL) and the outer segments are LPLG.

Biodegradable multi-arm star-block copolymers can be synthesized through ring opening polymerization. J. Biomater. Sci. Polymer Edn., Vol. 17, 2006, 615-630. In some embodiments, a star-block copolymer, such as P(CL-co-TMC)-b-PLLA, P(GA-co-CL)-b-PLLA, P(CL-co-TMC)-b-LPLG, or P(GA-co-CL)-b-LPLG, can be formed by solution-based polymerization. Other methods used to form the star-block copolymers are also possible, such as, without limitation, melt phase polymerization. In solution-based polymerization, all the reactive components involved in the polymerization reaction are dissolved in a solvent.

Figure 5:
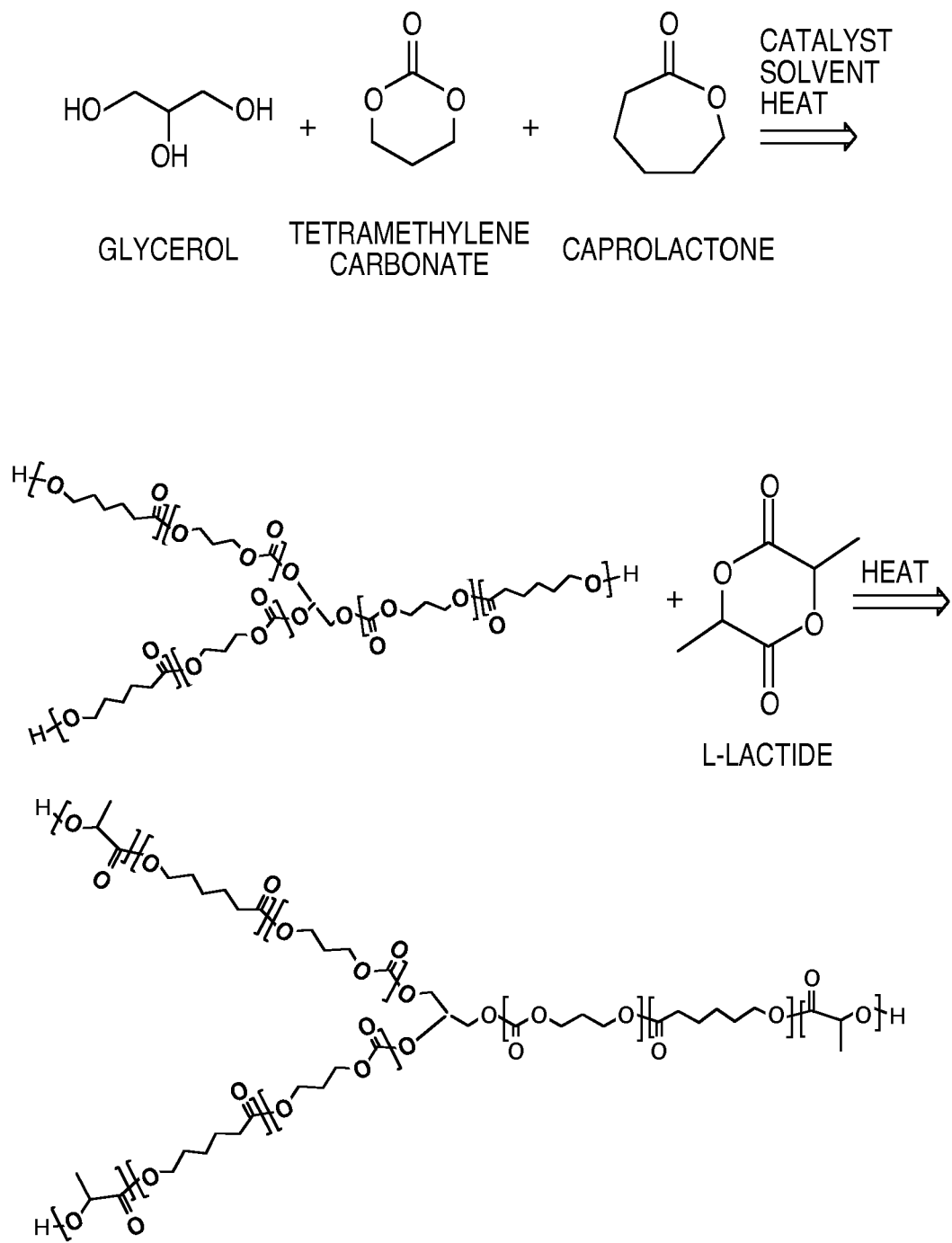
FIG. 5 depicts a synthesis scheme of a star-block copolymer.

To prepare P(CL-co-TMC)-b-PLLA star-block copolymer, a precursor P(CL-co-TMC) star copolymer may be prepared first by solution polymerization. The P(CL-co-TMC) star copolymer is then employed as a macro-initiator to initiate the polymerization of L-lactide monomers to form the PLLA outer segments. This scheme is illustrated in FIG. 5. Specifically, P(CL-co-TMC) star copolymer is formed first by mixing glycerol, CL units, and TMC units with a solvent to form a solution. In the solution, the glycerol, CL, and TMC units react to form a three arm P(GA-co-CL) star copolymer. L-lactide monomers are added to the solution or another solution containing the formed P(CL-co-TMC) star copolymer. The L-lactide monomers react with P(CL-co-TMC) star copolymer to form P(CL-co-TMC)-b-PLLA star-block copolymer.

To prepare P(GA-co-CL)-b-PLLA star-block copolymer, precursor P(GA-co-CL) star copolymer is formed first in a solution containing a solvent with GA units, CL units, and pentaerythritol. L-lactide monomers are then added to the solution to react with P(GA-co-CL) star copolymer to form P(GA-co-CL)-b-PLLA star block copolymer.

To prepare P(CL-co-TMC)-b-LPLG star-block copolymer, precursor P(CL-co-TMC) star copolymer is formed first in a solution containing a solvent with CL units, TMC units, and glycerol. L-lactide and GA units are then added to the solution to react with P(CL-co-TMC) star copolymer to form P(CL-co-TMC)-b-LPLG star-block copolymer.

The solvent(s) for forming the outer segments can be selected so that the star copolymer precursor is soluble in the solvent(s) to enable the precursor copolymer to copolymerize with outer segment units.

In other embodiments, star-block copolymers can be formed by reacting precursor star copolymers swollen with a solvent that contain outer segment units. The precursor star copolymer is swollen by a solvent after it is formed so that it can react with outer segment units. One of skill in the art can select a solvent that swells but does not dissolve the precursor star copolymer.

In one embodiment, the solvent for use in synthesizing the copolymer is devoid of alcohol functional groups. Such alcohol groups may act as initiators for chain growth in the polymer. Solvents used to synthesize the star-block copolymer include, but are not limited to, chloroform, toluene, xylene, and cyclohexane.

In some embodiments, the polymer blend of the matrix polymer and the star-block copolymer can be formed by solution blending, melt blending, or a combination thereof. The matrix polymer can be co-extruded with the polymer blend. The extruded polymer blend may be formed into a polymer construct, such as a tube or sheet which can be rolled or bonded to form a construct such as a tube. An implantable medical device may then be fabricated from the construct. For example, a stent can be fabricated from a tube by laser machining a pattern in to the tube. In another embodiment, a polymer construct may be formed from the polymer blend using an injection molding apparatus.

In general, representative examples of polymers that may be used in embodiments of the present invention include, but are not limited to, poly(N-acetylglucosamine) (Chitin), Chitosan, poly(hydroxyvalerate), poly(lactide-co-glycolide), poly(hydroxybutyrate), poly(hydroxybutyrate-co-valerate), polyorthoester, polyanhydride, poly(glycolic acid), poly (glycolide), poly(L-lactic acid), poly(L-lactide), poly(D,L-lactic acid), poly(L-lactide-co-glycolide); poly(D,L-lactide), poly(caprolactone), poly(trimethylene carbonate), polyethylene amide, polyethylene acrylate, poly(glycolic acid-co-trimethylene carbonate), co-poly(ether-esters) (e.g. PEO/PLA), polyphosphazenes, biomolecules (such as fibrin, fibrinogen, cellulose, starch, collagen and hyaluronic acid), polyurethanes, silicones, polyesters, polyolefins, polyisobutylene and ethylene-alphaolefin copolymers, acrylic polymers and copolymers other than polyacrylates, vinyl halide polymers and copolymers (such as polyvinyl chloride), polyvinyl ethers (such as polyvinyl methyl ether), polyvinylidene halides (such as polyvinylidene chloride), polyacrylonitrile, polyvinyl ketones, polyvinyl aromatics (such as polystyrene), polyvinyl esters (such as polyvinyl acetate), acrylonitrile-styrene copolymers, ABS resins, polyamides (such as Nylon 66 and polycaprolactam), polycarbonates, polyoxymethylenes, polyimides, polyethers, polyurethanes, rayon, rayon-triacetate, cellulose, cellulose acetate, cellulose butyrate, cellulose acetate butyrate, cellophane, cellulose nitrate, cellulose propionate, cellulose ethers, and carboxymethyl cellulose.

Additional representative examples of polymers that may be especially well suited for use in embodiments of the present invention include ethylene vinyl alcohol copolymer (commonly known by the generic name EVOH or by the trade name EVAL), poly(butyl methacrylate), poly(vinylidene fluoride-co-hexafluororpropene) (e.g., SOLEF 21508, available from Solvay Solexis PVDF, Thorofare, N.J.), polyvinylidene fluoride (otherwise known as KYNAR, available from ATOFINA Chemicals, Philadelphia, Pa.), ethylene-vinyl acetate copolymers, and polyethylene glycol.

For the purposes of the present invention, the following terms and definitions apply:

For the purposes of the present invention, the following terms and definitions apply:

The "glass transition temperature," Tg, is the temperature at which the amorphous domains of a polymer change from a brittle vitreous state to a solid deformable, ductile, or rubbery state at atmospheric pressure. In other words, the Tg corresponds to the temperature where the onset of segmental motion in the chains of the polymer occurs. When an amorphous or semicrystalline polymer is exposed to an increasing temperature, the coefficient of expansion and the heat capacity of the polymer both increase as the temperature is raised, indicating increased molecular motion. As the temperature is raised the actual molecular volume in the sample remains constant, and so a higher coefficient of expansion points to an increase in free volume associated with the system and therefore increased freedom for the molecules to move. The increasing heat capacity corresponds to an increase in heat dissipation through movement.

Tg of a given polymer can be dependent on the heating rate and can be influenced by the thermal history of the polymer. Furthermore, the chemical structure of the polymer heavily influences the glass transition.

"Stress" refers to force per unit area, as in the force acting through a small area within a plane. Stress can be divided into components, normal and parallel to the plane, called normal stress and shear stress, respectively. True stress denotes the stress where force and area are measured at the same time. Conventional stress, as applied to tension and compression tests, is force divided by the original gauge length.

"Strength" refers to the maximum stress along an axis which a material will withstand prior to fracture. The ultimate strength is calculated from the maximum load applied during the test divided by the original cross-sectional area.

"Modulus" may be defined as the ratio of a component of stress or force per unit area applied to a material divided by the strain along an axis of applied force that results from the applied force taken at very low strain where the stress-strain curve is linear. For example, a material has both a tensile and a compressive modulus. A material with a relatively high modulus tends to be stiff or rigid. Conversely, a material with a relatively low modulus tends to be flexible. The modulus of a material depends on the molecular composition and structure, temperature of the material, amount of deformation, and the strain rate or rate of deformation. For example, below its Tg, a polymer can be brittle with a high modulus. As the temperature of a polymer is increased from below to above its Tg, its modulus decreases by approximately 5 orders of magnitude.

"Strain" refers to the amount of elongation or compression that occurs in a material at a given stress or load.

"Elongation" may be defined as the increase in length in a material which occurs when subjected to stress. It is typically expressed as a percentage of the original length.

"Toughness" is the amount of energy absorbed prior to fracture, or equivalently, the amount of work required to fracture a material. One measure of toughness is the area under a stress-strain curve from zero strain to the strain at fracture. Thus, a brittle material tends to have a relatively low toughness.

"Solvent" is defined as a substance capable of dissolving or dispersing one or more other substances or capable of at least partially dissolving or dispersing the substance(s) to form a uniformly dispersed solution at the molecular- or ionic-size level at a selected temperature and pressure. The solvent should be capable of dissolving at least 0.1 mg of the polymer in 1 ml of the solvent, and more narrowly 0.5 mg in 1 ml at the selected temperature and pressure, for example, ambient temperature and ambient pressure.

EXAMPLES

The examples set forth below are for illustrative purposes only and are in no way meant to limit the invention. The following examples are given to aid in understanding the invention, but it is to be understood that the invention is not limited to the particular materials or procedures of examples.

Example 1

The following prophetic example illustrates the synthesis of a multi-arm star copolymer: P(CL-co-TMC)-b-PLLA. In this example the following are used: CL, TMC, and L-lactide (LLA) as monomers; stannous octoate as catalyst; propane-1,2,3-triol (glycerol) as initiator; and xylene as solvent. The proposed synthesis is as follows:

Step 1: One 2-Liter (L) reactor with a mechanical stirring rod is placed in a sealed glove box filled with high purity nitrogen. The reactor is preheated to 120° C. for 1 h and purged with high purity nitrogen to remove the moisture and oxygen.

Step 2: A mixture of 100 g CL, 100 g TMC, 92 mg glycerol, 500 mL xylene, and 704 mg stannous octoate is added into the reactor. The solution in the reactor is then stirred at 120° C. for between 70 h and 120 h.

Step 3: 100 g LLA and 280 mg additional catalyst is then added into the reactor. The mixture is stirred at 120° C. for up to 70 h.

Step 4: Once the polymerization is finished, 1 L $CHCl_3$ is added into reactor to dilute the final product. Then the final product is precipitated into 4-L methanol and dried in vacuum at 80° C. until constant weight is achieved.

Example 2

The following prophetic example illustrates preparation of a blend of the multi-arm copolymer synthesized in Example 1 and PLLA and preparation of a stent from the blend:

Step 1: Break P(CL-co-TMC)-b-PLLA star copolymer obtained in Example 1 into small pieces in a blender or a cryomiller.

Step 2: Mix PLLA and star copolymer (100:10) through solution blending or mechanical blending.

Step 3: Extrude PLLA/star copolymer mixture through a signal/twin screw extruder at a temperature to minimize the degradation of PLLA.

Step 4: Prepare stent from extruding tubing.

Example 3

The following prophetic example illustrates the synthesis of a multi-arm star copolymer: P(GA-co-CL)-b-PLLA. In this example the following are used: CL, GA, and LLA as monomers; stannous octoate as catalyst; pentaerythritol as initiator; and xylene as solvent. The proposed synthesis is as follows:

Step 1: 30 g GA, 20 g CL, 0.035 g pentaerythritol, and 100 ml xylene are added into a reactor free of moisture and oxygen.

Step 2: 100 mg stannous octoate are added after the temperature has increased to 100° C. The solution will become very viscous.

Step 3: Approximately 24 h later, 25 g LLA, and 0.14 mL catalyst are added.

Step 4: Approximately 96 h later, the final product can be precipitated into methanol and dried in a vacuum oven overnight.

Example 4

The following prophetic example illustrates the synthesis of a multi-arm star copolymer: P(CL-co-TMC)-b-LPLG. In this example the following are used: CL, GA, TMC, and LLA as monomers; stannous octoate as catalyst; glycerol as initiator; and xylene as solvent. The proposed synthesis is as follows:

Step 1: 100 g CL, 100 g TMC, 92 mg glycerol, 500 mL xylene are added into a reactor free of moisture and oxygen.

Step 2: 704 mg stannous octoate are added after the temperature has increased to 120° C. The polymerization solution is stirred at 120° C. for 72 h.

Step 3: 95 g LLA, 5 g GA, and 280 mg stannous octoate are added into the reactor.

Step 4: Approximately 48 h later, the final product is precipitated into methanol and dried in a vacuum oven overnight.

Example 5

The following prophetic example illustrates the synthesis of a multi-arm star copolymer: P(GA-co-CL)-b-LPLG. In this example the following are used: CL, GA, and LLA as monomers; stannous octoate as catalyst; pentaerythritol as initiator; and xylene as solvent. The proposed synthesis is as follows:

Step 1: 30 g GA, 20 g CL, 0.035 g pentaerythritol, and 100 ml xylene are added into a reactor free of moisture and oxygen.

Step 2: 100 mg stannous octoate are added after the temperature has increased to 100° C. The solution will become very viscous.

Step 3: Approximately 72 h later 23.75 g LLA, 1.25 g GA, and 0.14 mL catalyst are added.

Step 4: Approximately 48 h later, the final product is precipitated into methanol and dried in a vacuum oven overnight.

Example 6

The following prophetic example illustrates preparation of a blend of P(TMC-co-CO)-b-LPLG (Example 4) or P(GA-co-CL)-b-LPLG (Example 5) and LPLG and preparation of a stent from the blend:

Step 1: Break P(CL-co-TMC)-b-LPLG or P(GA-co-CL)-b-LPLG star copolymer into small pieces and mix with LPLG with 5 wt % GA content in a blender.

Step 2: Extrude the mixture of LPLG/star copolymer (100:10 weight ratio) through signal or twin screw extruder.

Step 3: Radially expand the extruded tubing and cut into stent with a laser.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. An implantable medical device fabricated from a polymer blend comprising:
   a biodegradable matrix polymer blended with biodegradable star-block copolymers having at least three arms, wherein the arms include inner segments and outer segments, the inner segments forming a discrete phase within a continuous phase, the continuous phase including the matrix polymer and the outer segments.

2. The device of claim 1, wherein the implantable medical device is a stent.

3. The device of claim 1, wherein the star-block copolymers are dispersed throughout the polymer matrix.

4. The device of claim 1, wherein the inner segments are faster degrading than the outer segment.

5. The device of claim 1, wherein the outer segments are of the same or similar chemical composition as the matrix polymer.

6. The device of claim 1, wherein the inner segments have a Tg below body temperature and the outer segments have a Tg above body temperature.

7. The device of claim 1, wherein the inner segments are elastic at physiological conditions.

8. The device of claim 1, wherein the outer segments are glassy at physiological conditions.

9. The device of claim 1, wherein the matrix polymer and the outer segments comprise PLLA.

10. An implantable medical device fabricated from a polymer blend comprising:
    a biodegradable matrix polymer blended with biodegradable star-block copolymers having at least three arms, wherein the arms include inner segments and outer segments, the inner segments forming a discrete phase within a continuous phase, the continuous phase including the matrix polymer and the outer segments,
    wherein the inner segments comprise units selected from the group consisting of CL, TMC, and dioxanone.

11. An implantable medical device fabricated from a polymer blend comprising:
    a biodegradable matrix polymer blended with biodegradable star-block copolymers having at least three arms, wherein the arms include inner segments and outer segments, the inner segments forming a discrete phase within a continuous phase, the continuous phase including the matrix polymer and the other segments,
    wherein the star-block copolymer comprises P(CL-co-TMC)-b-PLLA.

12. The device of claim 1, wherein 1 to 20 wt % of the polymer blend comprises the star-block copolymer.

13. The device of claim 10, wherein the implantable medical device is a stent.

14. The device of claim 10, wherein the star-block copolymers are dispersed throughout the polymer matrix.

15. The device of claim 10, wherein the inner segments are faster degrading than the outer segment.

16. The device of claim 10, wherein the outer segments are of the same or similar chemical composition as the matrix polymer.

17. The device of claim 10, wherein the inner segments have a Tg below body temperature and the outer segments have a Tg above body temperature.

18. The device of claim 10, wherein the inner segments are elastic at physiological conditions.

19. The device of claim 10, wherein the outer segments are glassy at physiological conditions.

20. The device of claim 10, wherein the matrix polymer and the outer segments comprise PLLA.

21. The device of claim 10, wherein 1 to 20 wt% of the polymer blend comprises the star-block copolymer.

* * * * *